United States Patent [19]

Doussain et al.

[11] Patent Number: 4,950,811

[45] Date of Patent: Aug. 21, 1990

[54] PROCESS FOR THE PREPARATION OF TRIFLUORO-ETHANOL BY HYDROLYSIS, IN THE GAS PHASE, OF CHLOROTRIFLUOROETHANE

[75] Inventors: Claude Doussain, Saint Fons; Michel Gubelmann, Lyons; Philippe-Jean Tirel, Oullins, all of France

[73] Assignee: Rhone Poulenc Chimie, Courbevoie, France

[21] Appl. No.: 388,936

[22] Filed: Aug. 3, 1989

[30] Foreign Application Priority Data

Aug. 5, 1988 [FR] France .............................. 88 10813

[51] Int. Cl.$^5$ ............................................ C07H 31/38
[52] U.S. Cl. ............................................... 568/842
[58] Field of Search ....................................... 568/842

[56] References Cited

U.S. PATENT DOCUMENTS 2,868,846  1/1959  Lawlor et al. ................... 568/842
4,434,297  2/1984  Astrologes ....................... 568/842

Primary Examiner—Howard T. Mars
Attorney, Agent, or Firm—Finnegan, Henderson, Farabow, Garrett and Dunner

[57] ABSTRACT

A process for the preparation of trifluoroethanol by hydrolysis, in the gas phase, of chlorotrifluoroethane. A gaseous mixture of 1-chloro-2,2,2-trifluoroethane and water is contacted with a solid catalyst and taken to a temperature greater than 350° C. and preferably between 400° and 500° C. 2,2,2-Trifluoroethanol (TFE) is a trifluorinated alcohol possessing very good thermal stability, which makes it suitable for a certain number of applications, in particular in the synthesis of fluorinated anesthetics, in pharmacology in general, and as a solvent.

16 Claims, No Drawings

PROCESS FOR THE PREPARATION OF TRIFLUORO-ETHANOL BY HYDROLYSIS, IN THE GAS PHASE, OF CHLOROTRIFLUOROETHANE

FIELD OF THE INVENTION

The present invention relates to a process for the preparation of trifluoroethanol by hydrolysis, in the gas phase, of chlorotrifluoroethane.

BACKGROUND OF THE INVENTION 2,2,2-Trifluoroethanol (TFE) is a trifluorinated alcohol possessing very good thermal stability, which makes it suitable for a certain number of applications, in particular in the synthesis of fluorinated anesthetics, in pharmacology in general, and as a solvent.

The preparation of this alcohol either by hydrogenation of trifluoroacetic acid or its esters, or by hydrolysis of 2,2,2-trifluoroethyl acetate, in the liquid phase in a solvent having hydroxyl groups, has been described in the prior art.

These various processes for the preparation of TFE are not entirely satisfactory on the industrial scale and, therefore, research has been undertaken in order to find out if it would be possible to carry out a direct hydrolysis, in the gas phase, of 1-chloro-2,2,2-trifluoroethane.

DESCRIPTION OF THE INVENTION

It is an objective of the present invention to prepare trifluoroethanol by hydrolysis, in the gas phase, of chlorotrifluoroethane.

The success of this hydrolysis is surprising, because it is known to those skilled in the art that the electro-attractive power of the $CF_3$ group of the 1-chloro-2,2,2-trifluoroethane molecule reduces, or renders very difficult, the possibility of attacking the carbon atom, which is linked to the chlorine, of this molecule with a nucleophilic compound.

The process according to the invention for the preparation of trifluoroethanol by hydrolysis of trifluorochlorethane comprises contacting a mixture of 1-chloro-2,2,2-trifluoroethane and water with a solid catalyst comprising at least one phosphate, one hydrophosphate, or one oxide of a di- or trivalent metal, at a temperature greater than 350° C. and preferably between 400 and 500° C.

The phosphates which are suitable catalyst components are the salts of phosphoric acid of a di- or trivalent metal, including the rare-earth metals. Suitable hydrophosphates are the salts of phosphoric acid of a di- or trivalent metal, including the rare earth metals, in which at least one hydrogen atom has been replaced by a metal atom. Suitable oxides are known compounds.

Among these catalysts, one preferred catalyst is lanthanum phosphate, $LaPO_4$; this lanthanum phosphate is a compound of high purity which is commercially available.

The temperature must be at least 350° C. Below this temperature no reaction is detected. The examples were carried out in a Pyrex glass reactor and, therefore, it was not believed possible to work at temperatures greater than about 500° C. It appeared that at the highest temperatures used, the existence of extraneous reactions was detected.

The reaction may be carried out batchwise or continuously. In the preferred process, it is carried out continuously. For the continuous reaction, the gaseous mixture is passed over the catalyst, which has been taken to the chosen temperature, and the products emerging are then collected by a simple cold trap. The contact time between the gaseous mixture and the catalyst may be very short; it is generally between 1 and 10 seconds.

Finally, the relative proportions of water and 1-chloro-2,2,2-trifluoroethane are, in moles, between 1 and 15. It is possible, if desirable, to add an inert gas such as nitrogen to the gaseous mixture, providing a certain amount of dilution.

The following non-limiting examples illustrate the invention.

These examples were carried out according to the following experimental protocol:

the catalytic solid (the mean particle size of which was 1 mm) was introduced into a tubular Pyrex glass reactor (said reactor having an internal diameter of 1.8 cm and a total length of 16 cm), a bed of glass beads was deposited on the surface of the bed of catalytic solid, the whole was heated to the desired reaction temperature for one-half hour, then the mixture of gaseous reactants (water and 1-chloro-2,2,2,-trifluoroethane) was circulated in the tube (entering from the side on which the bed of glass beads was located). When reaction equilibrium had been established, the gases emerging from the reactor were trapped, and the products obtained were analyzed by gas phase chromatography (the structures of the products were confirmed by mass spectrometry).

The results obtained are given in the following Table 1.

Examples 7 and 8 show that, at 490° C. and a contact time of the order of 2 seconds, 19% of the 1-chloro-2,2,2-trifluoroethane was converted to 11% (with respect to the 1-chloro-2,2,2-trifluoroethane used in the reactor) TFE, with a selectivity (RT) of 60 to 70%, defined as being the number of moles of TFE obtained with respect to the number of moles of 1-chloro-2,2,2-trifluoroethane converted.

TABLE 1

| Example | Catalyst | Temperature (°C.) | Molar ratio $H_2O$/chlorotrifluoroethane | Contact time (sec) | Degree of conversion of 1-chloro-2,2,2-trifluoroethane (%) | Yield of TFE | Selectivity for TFE (%) |
|---|---|---|---|---|---|---|---|
| 1 | $LaPO_4$ | 350 | 2 | 2 | — | 1 | — |
| 2 | $LaPO_4$ | 400 | 2 | 2 | — | 2 | — |
| 3 | $LaPO_4$ | 450 | 2 | 2 | — | 4.9 | — |
| 4 | $LaPO_4$ | 450 | 2 | 3 | — | 3.4 | — |
| 5 | $LaPO_4$ | 450 | 5 | 2 | 13 | 7.6 | 59 |
| 6 | $LaPO_4$ | 450 | 10 | 1 | 11 | 6.1 | 56 |
| 7 | $LaPO_4$ | 490 | 5 | 2 | 19 | 11.7 | 62 |
| 8 | $LaPO_4$ | 490 | 5 | 2 | 19 | 11.3 | 60 |
| 9 | $LaPO_4$ | 490 | 10 | 1 | 19 | 8.7 | 46 |

TABLE 1-continued

| Example | Catalyst | Temperature (°C.) | Molar ratio H₂O/chloro-trifluoro-ethane | Contact time (sec) | Degree of conversion of 1-chloro-2,2,2-trifluoro-ethane (%) | Yield of TFE | Selectivity for TFE (%) |
| --- | --- | --- | --- | --- | --- | --- | --- |
| 10 | Ca₃(PO₄)₂ | 450 | 5 | 2 | — | 1 | — |

What is claimed is:

1. A process for the preparation of trifluoroethanol by hydrolysis of trifluorochlorethane which comprises contacting a gaseous mixture of 1-chloro-2,2,2-trifluoroethane and water with a solid catalyst comprising at least one phosphate, one hydrophosphate, or one oxide of a di- or trivalent metal, at a temperature greater than 350° C.

2. The process according to claim 1, wherein the temperature is from 400 to 500° C.

3. The process according to claim 2, wherein the contact time between said gaseous mixture and said solid catalyst is between 1 and 10 seconds.

4. The process according to claim 1, wherein the contact time between said gaseous mixture and said solid catalyst is between 1 and 10 seconds.

5. The process according to claim 4, wherein the water and the 1-chloro-2,2,2-trifluorothane are present in a molar ratio of from 1 to 15.

6. The process according to claim 3, wherein the water and the 1-chloro-2,2,2-trifluorothane are present in a molar ratio of from 1 to 15.

7. The process according to claim 2, wherein the water and the 1-chloro-2,2,2-trifluorothane are present in a molar ratio of from 1 to 15.

8. The process according to claim 1, wherein the water and the 1-chloro-2,2,2-trifluorothane are present in a molar ratio of from 1 to 15.

9. The process according to claim 8, wherein the catalyst is lanthanum phosphate.

10. The process according to claim 7, wherein the catalyst is lanthanum phosphate.

11. The process according to claim 6, wherein the catalyst is lanthanum phosphate.

12. The process according to claim 5, wherein the catalyst is lanthanum phosphate.

13. The process according to claim 4, wherein the catalyst is lanthanum phosphate.

14. The process according to claim 3, wherein the catalyst is lanthanum phosphate.

15. The process according to claim 2, wherein the catalyst is lanthanum phosphate.

16. The process according to claim 1, wherein the catalyst is lanthanum phosphate.

* * * * *